US009421273B2

(12) United States Patent
Chao

(10) Patent No.: US 9,421,273 B2
(45) Date of Patent: Aug. 23, 2016

(54) SILICON-CONTAINING FUMARIC ACID ESTERS

(71) Applicant: Biogen Idec MA Inc., Cambridge, MA (US)

(72) Inventor: Jianhua Chao, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/363,546

(22) PCT Filed: Dec. 14, 2012

(86) PCT No.: PCT/US2012/069872
§ 371 (c)(1),
(2) Date: Jun. 6, 2014

(87) PCT Pub. No.: WO2013/090799
PCT Pub. Date: Jun. 20, 2013

(65) Prior Publication Data
US 2014/0336151 A1    Nov. 13, 2014

Related U.S. Application Data

(60) Provisional application No. 61/576,828, filed on Dec. 16, 2011.

(51) Int. Cl.
C07F 7/04 (2006.01)
A61K 47/48 (2006.01)
C07F 7/08 (2006.01)
C07F 7/18 (2006.01)

(52) U.S. Cl.
CPC ....... A61K 47/48023 (2013.01); C07F 7/0836 (2013.01); C07F 7/184 (2013.01); C07F 7/1836 (2013.01); C07F 7/1896 (2013.01)

(58) Field of Classification Search
CPC ............................ C08F 4/444; C07F 7/1896
USPC ........................................................ 556/446
See application file for complete search history.

(56) References Cited

U.S. PATENT DOCUMENTS 5,436,284 A * 7/1995 Honda .................. C09D 143/04
                                                           106/15.05
2006/0241240 A1   10/2006 Vos et al.
2009/0011986 A1    1/2009 Joshi et al.
2009/0306015 A1   12/2009 Gately et al.

FOREIGN PATENT DOCUMENTS

DE    102007042948 A1    3/2009
JP       S62 235919 A   10/1987
JP       H02 126927 A    5/1990
WO    WO 2008/097596 A2   8/2008
WO    WO 2009/147024 A1  12/2009
WO    WO 2010/126605 A1  11/2010

OTHER PUBLICATIONS

International Search Report, PCT/US 12/69872, Feb. 26, 2013.*
Bell et al., 2009, "Synthesis of the first C2-asymmetric phosphinine and its pyrylium precursor," Tetrahedron, 65(45):9368-9372.
Borshell et al., 2011, "Deal watch: Is deal-making becoming more difficult?," Nat. Rev. Drug Discov., 10(6):404.
Calkins et al., 2009, "The Nrf2/ARE pathway as a potential therapeutic target in neurodegenerative disease," Antioxid. Redox Signal, 11(3);497-508.
Coelho et al., 2000, "Intramolecular Diels-Adler Reaction of Chiral Silatrienes: Synthesis of 4a,7,8,8a-Tetrahyfro-4-silaisochroman-1-ones." Eur. J. Org. Chem., 2000(17):3039-3046.
Fedotov et al., 1982, "Some Reactions of 1[(Chloroorganosilyl)-Alkyl and -Aryl]- Adamantanes," Journal of General Chemistry translated from Zhurnal Obshchei Khimii 57(8):1837-1842.

(Continued)

Primary Examiner — Porfirio Nazario Gonzalez
Assistant Examiner — Kofi Adzamli
(74) Attorney, Agent, or Firm — Jones Day

(57) ABSTRACT

The present invention is directed to silicon-containing fumaric acid esters of the Formulae I-IV. The silicon-containing fumaric acid esters of Formulae I-IV are useful in transplantation medicine and for the treatment of autoimmune diseases and autoimmune-related diseases. (I), (II), (III) & (IV).

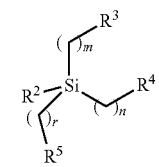

(I)

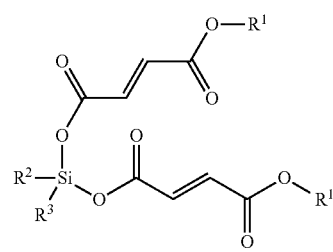

(II)

(III)

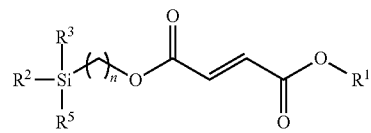

(IV)

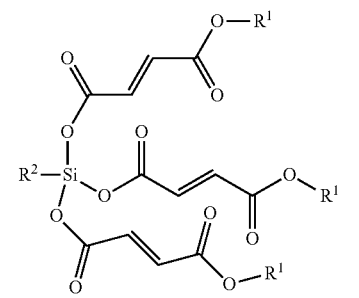

8 Claims, 3 Drawing Sheets

(56) References Cited

OTHER PUBLICATIONS

Haidet-Phillips et al., 2011, "Astrocytes from familial and sporadic ALS patients are toxic to motor neurons," Nat. Biotechnol., 29(9):824-828.

International Preliminary Report on Patentability for International Patent Application PCT/US2012/069872, mailed Jun. 26, 2014, International Bureau of WIPO, Switzerland.

International Search Report of International Application PCT/US2012/069872, mailed Feb. 26, 2012.

Jakel et al., 2007, "Nrf2-mediated protection against 6-hydroxydopamine," Brain Res., 1144:192-201.

Johansson et al., 2010 "In vitro metabolism of haloperidol and sila-haloperidol: new metabolic pathways resulting from carbon-silicon exchange," Drug Metab. Dispos., 38(1):73-83.

Kappos et al., 2008, "Efficacy and safety of oral fumarate in patients with relapsing-remitting multiple sclerosis: a multicentre, randomised, double-blind, placebo-controlled phase IIb study," Lancet., 372:1463-1472.

Pooni et al., 2006, "Silicon switches of marketed drugs," Mini Rev. Med. Chem., 6(10):1169-1177.

Sobel et al., 1984, "The Immunopathology of Experimental Allergic Encephalomyelitis. I. Quantitative Analysis of Inflammatory Cells In Situ," J. Immunol., 132(5):2393-2401.

Stack et al., 2010, "Triterpenoids CDDO-ethyl amide and CDDO-trifluoroethyl amide improve the behavioral phenotype and brain pathology in a transgenic mouse model of Huntington's disease," Free Radic. Biol. Med., 49(2):147-158.

Traugott et al., 1989, "Detailed Analysis of Early Immunopathologic Events during Lesion Formation in Acute Experimental Autoimmune Encephalomyelitis," Cell. Immunol., 119:114-129.

Tuohy et al., 1988, "A Synthetic Peptide From Myelin Proteolipid Protien Induces Experimental Allergic Encephalomyelitis," J. Immunol., 141(4):1126-1130.

Vargas et al., 2008 "Nrf2 activation in astrocytes protects against neurodegenerative in mouse models of familial amyotrophic lateral sclerosis," J. Neurosci., 28(50):13574-13581.

Voronkov et al., 1982, "(Trialkylsilyl)- and (Trimethoxysilyl)-Methyl (Aryloxy)Acetates," Journal of General Chemistry translated from Zhurnal Obschchei Khimii 52(9):2052-2055.

Wegorzewska et al., 2009, "TDP-43 mutant transgenic mice develop features of ALS and frontotemporal lobar degeneration," Proc. Natl. Acad. Sci. USA, 106(44):18809-18814.

Wong et al., 1995, "An adverse property of a familial ALS-linked SOD1 mutation causes motor neuron disease characterized by vascuolar degeneration of mitochondria," Neuron 14(6):1105-1116.

Written Opinion of the International Searching Authority for International Patent Application PCT/US2012/069872, mailed Feb. 26, 2013.

Zhang et al., 2009, Synthesis and application of bulky phosphoramidites: highly effective monophosphorus ligands for asymmetric hydrosilylation of styrenes, Org. Biomol. Chem., 7(21):4470-4474.

Eritsyan et al., 1986, "Organosilicon bis(diallyl) derivatives of isocyanuric acid," Journal of General Chemistry of the USSR, 56(1):145-147; English translation of Zhurnal Obshchei Khimii, 56(1):166-169.

Extended European Search Report, including the supplementary European Search Report and the European Search Opinion, dated Jul. 3, 2015 for Application No. EP 12856877.

Lauchli et al., 2005, "Synthesis and Chemistry of Bridgehead Allylsilanes. Stereoselective Reactions with Aldehydes," Org. Lett. 7(18):3913-3916.

\* cited by examiner

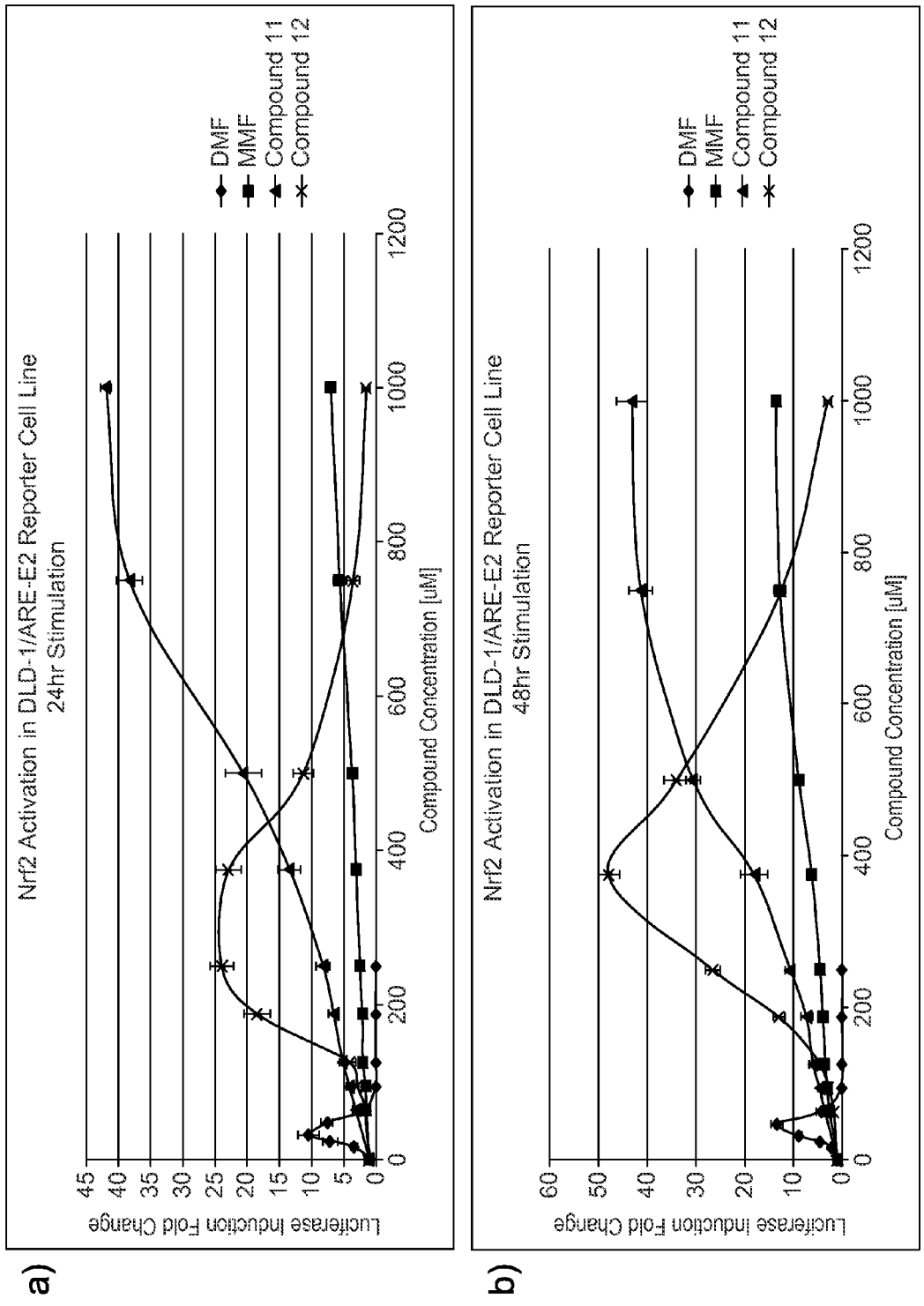

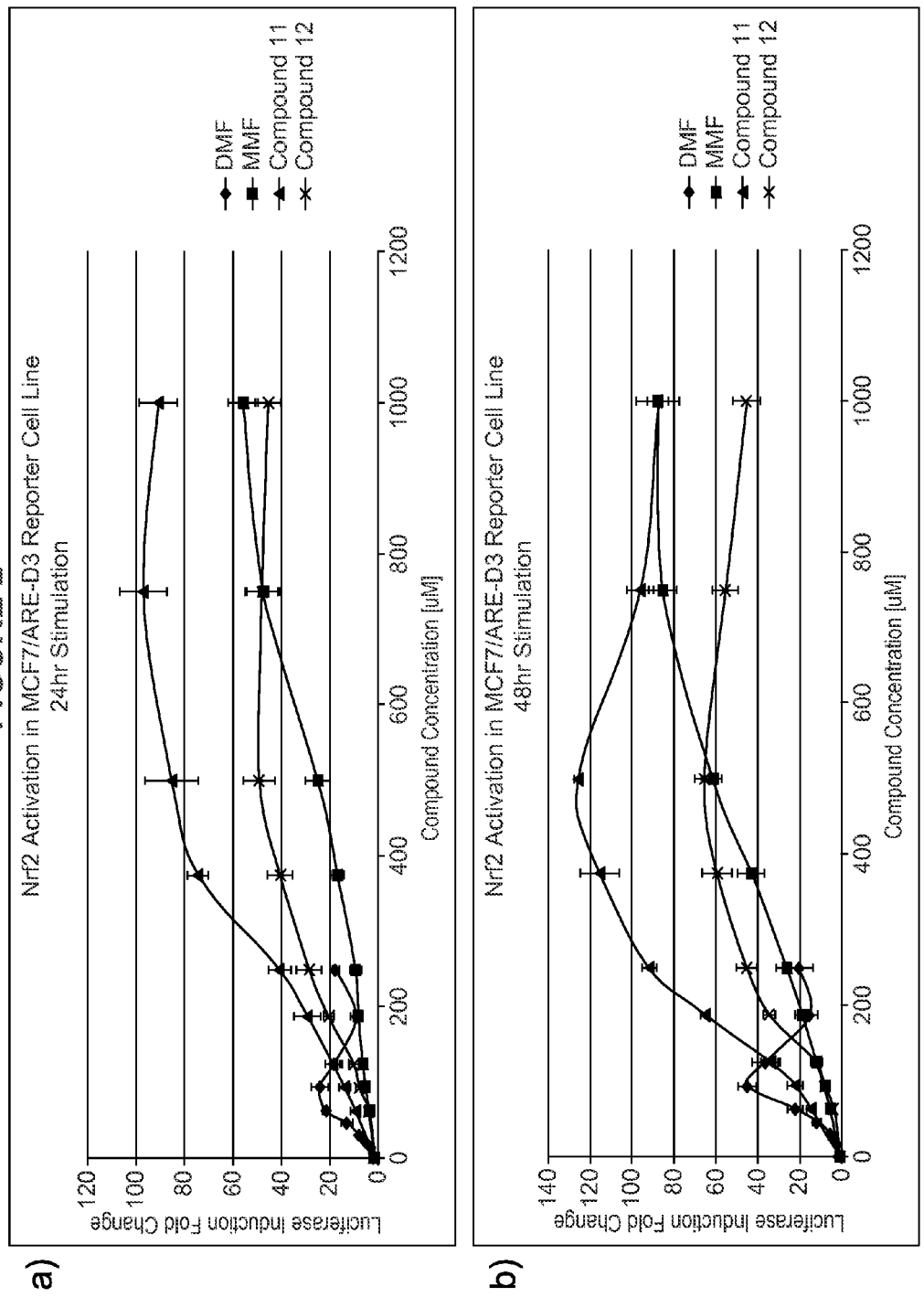

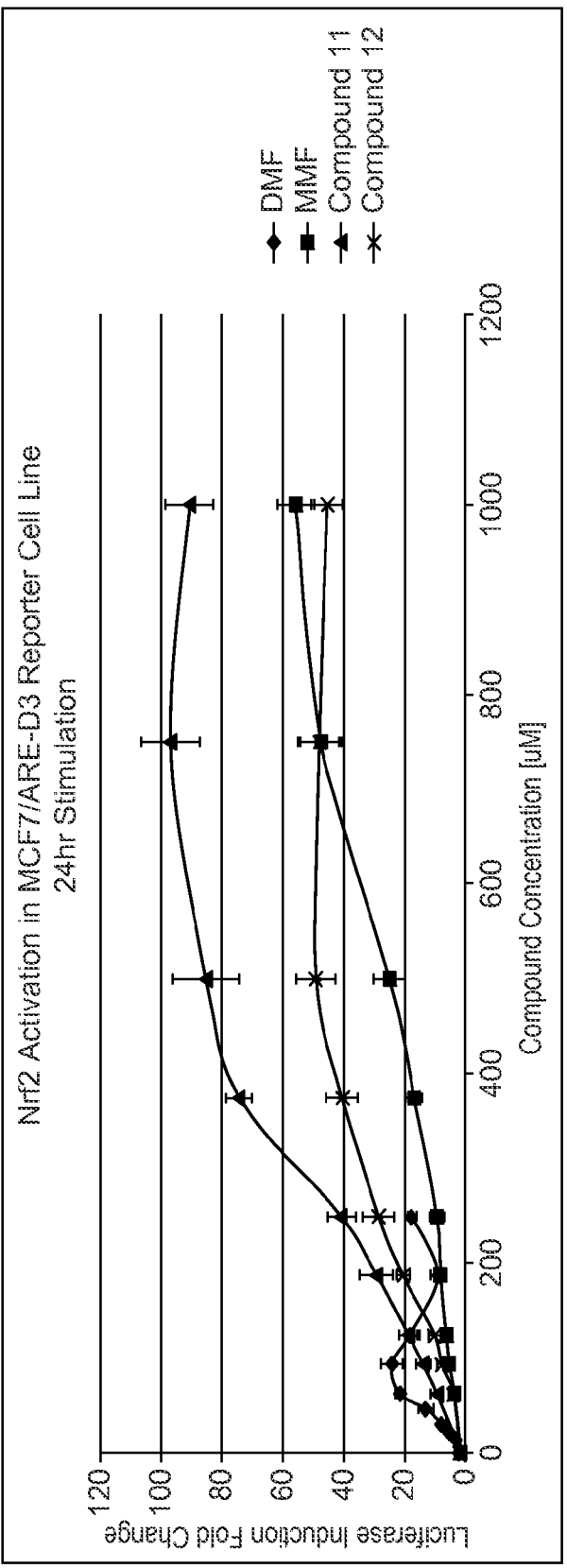

SILICON-CONTAINING FUMARIC ACID ESTERS

BRIEF SUMMARY OF THE INVENTION

The methods provided are exemplary and are not intended to limit the scope of the claimed embodiments.

In one embodiment, the present invention provides a compound of Formula I:

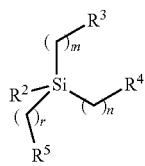

(I)

or a pharmaceutically acceptable salt thereof, wherein:
$R^2$ is $C_1$-$C_{10}$ alkyl, $C_6$-$C_{10}$ aryl, hydroxyl, —O—$C_1$-$C_{10}$ alkyl, or —O—$C_6$-$C_{10}$ aryl;
each of $R^3$, $R^4$, and $R^5$, independently, is $C_1$-$C_{10}$ alkyl, $C_6$-$C_{10}$ aryl, hydroxyl, —O—$C_1$-$C_{10}$ alkyl, —O—$C_6$-$C_{10}$ aryl, or

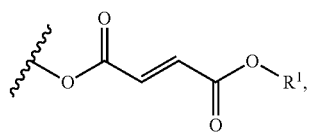

wherein $R^1$ is $C_1$-$C_{24}$ alkyl or $C_6$-$C_{10}$ aryl; each of which can be optionally substituted; and
each of m, n, and r, independently, is 0-4;
provided that at least one of $R^3$, $R^4$, and $R^5$ is

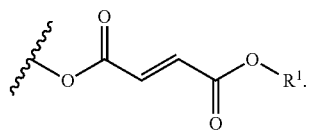

In another embodiment, the present invention provides a compound of Formula II:

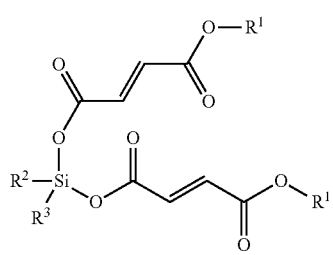

(II)

or a pharmaceutically acceptable salt thereof, wherein:
$R^1$ is $C_1$-$C_{24}$ alkyl or $C_6$-$C_{10}$ aryl; and
each of, independently, $R^2$ and $R^3$, is $C_1$-$C_{10}$ alkyl or $C_6$-$C_{10}$ aryl.

In one embodiment, the present invention provides a compound of Formula II, wherein $R^1$ is methyl, ethyl, or isopropyl. In another embodiment, the present invention provides a compound of Formula II wherein each of $R^2$ and $R^3$, independently, is methyl, ethyl, or isopropyl.

In another embodiment, the present invention provides a compound of Formula III:

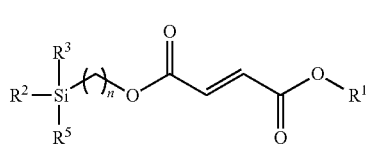

(III)

or a pharmaceutically acceptable salt thereof, wherein:
$R^1$ is $C_1$-$C_{24}$ alkyl or $C_6$-$C_{10}$ aryl;
each of $R^2$, $R^3$, and $R^5$, independently, is hydroxyl, $C_1$-$C_{10}$ alkyl, $C_6$-$C_{10}$ aryl, —O—$C_1$-$C_{10}$ alkyl, or —O—$C_6$-$C_{10}$ aryl; and
n is 1 or 2.

In one embodiment, the present invention provides a compound of Formula III, wherein each of $R^2$, $R^3$, and $R^5$, independently, is hydroxyl, methyl, or ethyl. In another embodiment, the present invention provides a compound of Formula III, wherein n is 1.

In another embodiment, the present invention provides a compound of Formula IV:

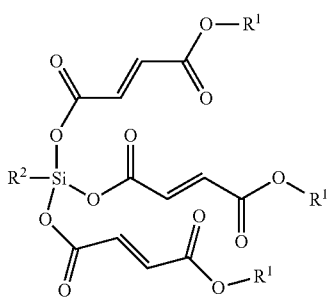

(IV)

or a pharmaceutically acceptable salt thereof, wherein:
$R^1$ is $C_1$-$C_{24}$ alkyl or $C_6$-$C_{10}$ aryl; and
$R^2$ is $C_1$-$C_{10}$ alkyl.

In one embodiment, the present invention provides a compound of Formula IV, wherein each $R^1$, independently, is is methyl, ethyl, or isopropyl. In another embodiment, the present invention provides a compound of Formula IV, wherein $R^2$ is methyl, ethyl, or isopropyl.

In another embodiment, the present invention provides a pharmaceutical composition comprising a pharmaceutically acceptable carrier and one or more compounds of Formula I, Formula II, Formula III, Formula IV, or mixtures thereof.

In another embodiment, the present invention provides a method of treating a subject having a condition characterized by at least one symptom chosen from neurodegeneration and neuroinflammation comprising administering to a subject a compound of Formula I:

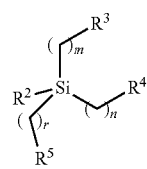

(I)

or a pharmaceutically acceptable salt thereof, wherein:
$R^2$ is $C_1$-$C_{10}$ alkyl, $C_6$-$C_{10}$ aryl, hydroxyl, —O—$C_1$-$C_{10}$ alkyl, or —O—$C_6$-$C_{10}$ aryl;

each of $R^3$, $R^4$, and $R^5$, independently, is $C_1$-$C_{10}$ alkyl, $C_6$-$C_{10}$ aryl, hydroxyl, —O—$C_1$-$C_{10}$ alkyl, —O—$C_6$-$C_{10}$ aryl, or

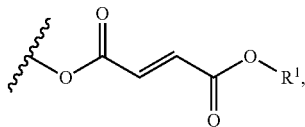

wherein $R^1$ is $C_1$-$C_{24}$ alkyl or $C_6$-$C_{10}$ aryl; each of which can be optionally substituted; and
each of m, n, and r, independently, is 0-4;
provided that at least one of $R^3$, $R^4$, and $R^5$ is

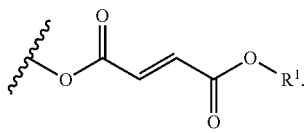

In another embodiment, the present invention provides a method of treating a subject having a condition characterized by at least one symptom chosen from neurodegeneration and neuroinflammation comprising administering to a subject a compound of Formula II:

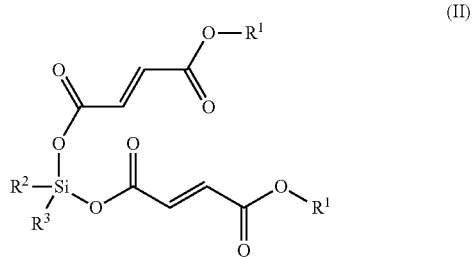

or a pharmaceutically acceptable salt thereof, wherein:
$R^1$ is $C_1$-$C_{24}$ alkyl or $C_6$-$C_{10}$ aryl; and
each of, independently, $R^2$ and $R^3$, is $C_1$-$C_{10}$ alkyl or $C_6$-$C_{10}$ aryl.

In another embodiment, the present invention provides a method of treating a subject having a condition characterized by at least one symptom chosen from neurodegeneration and neuroinflammation comprising administering to a subject a compound of Formula III:

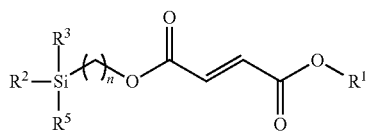

or a pharmaceutically acceptable salt thereof, wherein:
$R^1$ is $C_1$-$C_{24}$ alkyl or $C_6$-$C_{10}$ aryl;
each of $R^2$, $R^3$, and $R^5$, independently, is hydroxyl, $C_1$-$C_{10}$ alkyl, $C_6$-$C_{10}$ aryl, —O—$C_1$-$C_{10}$ alkyl, or —O—$C_6$-$C_{10}$ aryl; and
n is 1 or 2.

In another embodiment, the present invention provides a method of treating a subject having a condition characterized by at least one symptom chosen from neurodegeneration and neuroinflammation comprising administering to a subject a compound of Formula IV:

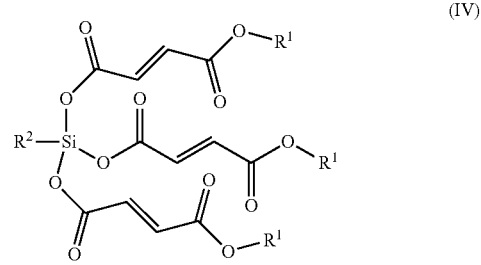

or a pharmaceutically acceptable salt thereof, wherein:
$R^1$ is $C_1$-$C_{24}$ alkyl or $C_6$-$C_{10}$ aryl; and
$R^2$ is $C_1$-$C_{10}$ alkyl.

In one embodiment, the present invention provides a method of treating a subject having a condition characterized by at least one symptom chosen from neurodegeneration and neuroinflammation wherein the condition is multiple sclerosis, Huntington's disease, Amyotrophic lateral sclerosis, Alzheimer's disease, or Parkinson's disease by administering a compound of Formula I, Formula II, Formula III, or Formula IV.

In one embodiment, the present invention provides a compound of Formula I selected from the group consisting of: (dimethylsilanediyl)dimethyl difumarate, methyl ((trimethoxysilyl)methyl) fumarate, methyl ((trihydroxysilyl)methyl) fumarate, and trimethyl (methylsilanetriyl)trifumarate.

BRIEF DESCRIPTION OF THE DRAWINGS

FIG. 1a provides the luciferase induction fold change after 24 hours of stimulation with the compounds dimethyl fumarate (DMF), monomethyl fumarate (MMF), (E)-O,O'-(dimethylsilanediyl)dimethyl difumarate (Compound 11), and methyl ((trimethoxysilyl)methyl) fumarate (Compound 12) based on compound concentration in the DLD-1/ARE-E2 cell reporter cell line.

FIG. 1b provides the luciferase induction fold change after 48 hours of stimulation with the compounds dimethyl fumarate (DMF), monomethyl fumarate (MMF), (E)-O,O'-(dimethylsilanediyl)dimethyl difumarate (Compound 11), and methyl ((trimethoxysilyl)methyl) fumarate (Compound 12) based on compound concentration in the DLD-1/ARE-E2 cell reporter cell line.

FIG. 2a provides the luciferase induction fold change after 24 hours of stimulation with the compounds dimethyl fumarate (DMF), monomethyl fumarate (MMF), (E)-O,O'-(dimethylsilanediyl)dimethyl difumarate (Compound 11), and methyl ((trimethoxysilyl)methyl) fumarate (Compound 12) based on compound concentration in the MCF7/ARE-D3 cell reporter cell line.

FIG. 2b provides the luciferase induction fold change after 48 hours of stimulation with the compounds dimethyl fumarate (DMF), monomethyl fumarate (MMF), (E)-O,O'-(dimethylsilanediyl)dimethyl difumarate (Compound 11), and methyl ((trimethoxysilyl)methyl) fumarate (Compound 12) based on compound concentration in the MCF7/ARE-D3 cell reporter cell line.

FIG. 3 provides the luciferase induction fold change after 24 hours of stimulation with the compounds dimethyl fumarate (DMF), monomethyl fumarate (MMF), (E)-O,O'-

(dimethylsilanediyl)dimethyl difumarate (Compound 11), and methyl ((trimethoxysilyl)methyl) fumarate (Compound 12) based on compound concentration in the MCF7/ARE-D3 cell reporter cell line.

DETAILED DESCRIPTION OF THE INVENTION

Dimethyl fumarate (DMF) has been shown to have significant therapeutic effects on patients having multiple sclerosis. See, e.g., Kappos et al., *Lancet* 372:1463-1472 (2008) and *Nature Drug Reviews* 10:404 (2011). Preclinical studies indicate that the therapeutic effects of DMF appear to be mediated through activation of the nuclear factor-E2-related factor 2 (Nrf2) transcriptional pathway, which is a major pathway to combat oxidative stress associated with several different neurological diseases (see, e.g., WO 2008/097596 and Calkins et al., *Antioxid. Redox Signal* 11(3):497-508 (2009)). DMF is rapidly metabolized into monomethyl fumarate (MMF) upon administration. The present invention discloses silicon-containing compounds, which like DMF, can metabolize into MMF upon administration.

The silicon atom, although similar to carbon, has a larger covalent radius ($r_{Si}$=117 pm) than carbon ($r_C$=77 pm) and therefore forms longer and slightly more flexible bonds which result in subtle changes in molecular size and shape of the silicon analogs. Furthermore, silicon is more electropositive which causes a slight change in bond polarization. These differences affect how silicon analogs interact with enzymes and proteins which could give rise to different pharmacological effects and metabolism. For example, silahaloperidol has shown lack of a major pyridinium metabolite, wherein this metabolite was directly linked to neurotoxic side effects observed by the carbon analog haloperidol. Johansson, T., et al., *Drug Metabolism & Disposition* 38:73-83 (2010).

Additionally, the fact that silicon is more electropositive would make it possible to differentiate between the two ester groups in the disclosed fumarate molecules. This would allow for regioselective hydrolysis of the silicon-containing ester group to occur and would unmask the active drug ingredient.

Silicon analogs are in general more lipophilic. A small increase in lipophilicity will markedly increase the absorption, volume of distribution, and tissue penetration of a drug, leading to a lesser degree of hepatic metabolism and enhance the plasma half-life of a drug. In addition, increasing lipophilicity may also improve the permeability through the blood brain barrier, enhancing central nervous system activity. See Pooni, P. K., et al., *Mini-Reviews in Med. Chem.* 6:1169-1177 (2006). The silyl group confers lipophilicity that can enhance the penetration of the compounds across the gut wall, cell membranes, and blood brain barrier, thus improving therapeutic properties including bioavailability, metabolism, and pharmacokinetics.

The present invention provides silicon-containing fumaric acid esters represented by Formula I:

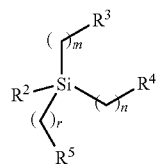

(I)

or a pharmaceutically acceptable salt thereof, wherein:
$R^2$ is $C_1$-$C_{10}$ alkyl, $C_5$-$C_{15}$ aryl, hydroxyl, —O—$C_1$-$C_{10}$ alkyl, or —O—$C_5$-$C_{15}$ aryl;

each of $R^3$, $R^4$, and $R^5$, independently, is $C_1$-$C_{10}$ alkyl, $C_5$-$C_{15}$ aryl, hydroxyl, —O—$C_1$-$C_{10}$ alkyl, —O—$C_5$-$C_{15}$ aryl, or

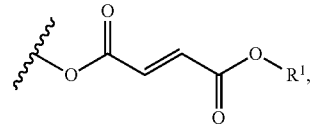

wherein $R^1$ is $C_1$-$C_{24}$ alkyl or $C_5$-$C_{50}$ aryl; each of which can be optionally substituted; and
each of m, n, and r, independently, is 0-4;
provided that at least one of $R^3$, $R^4$, and $R^5$ is

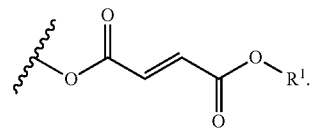

Another group of compounds of Formula I include compounds wherein $R^1$ is optionally substituted $C_1$-$C_{24}$ alkyl. Another group of compounds of Formula I include compounds wherein $R^1$ is optionally substituted $C_1$-$C_6$ alkyl. Another group of compounds of Formula I include compounds wherein $R^1$ is optionally substituted methyl, ethyl, or isopropyl. Another group of compounds of Formula I include compounds wherein $R^1$ is optionally substituted $C_5$-$C_{50}$ aryl. Another group of compounds of Formula I include compounds wherein $R^1$ is optionally substituted $C_5$-$C_{10}$ aryl. Another group of compounds of Formula I include compounds wherein $R^2$ is $C_1$-$C_{10}$ alkyl. Another group of compounds of Formula I include compounds wherein $R^2$ is optionally substituted $C_1$-$C_6$ alkyl. Another group of compounds of Formula I include compounds wherein $R^2$ is optionally substituted methyl, ethyl, or isopropyl. Another group of compounds of Formula I include compounds wherein $R^2$ is optionally substituted $C_5$-$C_{15}$ aryl. Another group of compounds of Formula I include compounds wherein $R^2$ is optionally substituted $C_5$-$C_{10}$ aryl.

In another embodiment, the invention provides compounds represented by Formula II:

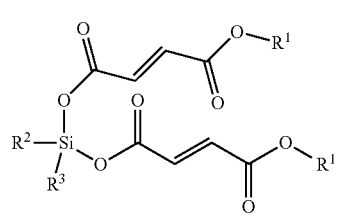

(II)

or a pharmaceutically acceptable salt thereof, wherein:
each of, independently, $R^2$ and $R^3$, is $C_1$-$C_{10}$ alkyl or $C_5$-$C_{15}$ aryl.
$R^2$ and $R^3$ can be the same or different, can be optionally substituted, and independently can be selected from the group consisting of $C_1$-$C_{10}$ alkyl or $C_5$-$C_{15}$ aryl.

In another embodiment, compounds of Formula II include compounds wherein $R^1$ is optionally substituted $C_1$-$C_{24}$ alkyl. Another group of compounds of Formula II include compounds wherein $R^1$ is optionally substituted $C_1$-$C_6$ alkyl. Another group of compounds of Formula II include compounds wherein R¹ is optionally substituted methyl, ethyl, or isopropyl. Another group of compounds of Formula II include compounds wherein R¹ is optionally substituted $C_5$-$C_{50}$ aryl. Another group of compounds of Formula II include compounds wherein R¹ is optionally substituted $C_5$-$C_{10}$ aryl. alkyl. Another group of compounds of Formula II include compounds wherein each of R² and R³ is, independently, optionally substituted $C_1$-$C_{10}$ alkyl. Another group of compounds of Formula II include compounds wherein each of R² and R³ is, independently, optionally substituted $C_1$-$C_6$ alkyl. Another group of compounds of Formula II include compounds wherein each of R² and R³ is, independently, optionally substituted methyl, ethyl, or isopropyl. Another group of compounds of Formula II include compounds wherein each of R² and R³ is, independently, optionally substituted $C_5$-$C_{15}$ aryl. Another group of compounds of Formula II include compounds wherein each of R² and R³ is, independently, optionally substituted $C_5$-$C_{10}$ aryl.

In another embodiment, the invention provides compounds represented by Formula III:

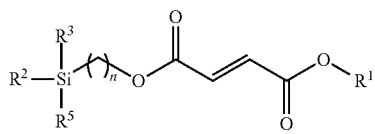

(III)

or a pharmaceutically acceptable salt thereof, wherein:
R¹ is $C_1$-$C_{24}$ alkyl or $C_5$-$C_{50}$ aryl;
each of R², R³, and R⁵, independently, is hydroxyl, $C_1$-$C_{10}$ alkyl, $C_5$-$C_{15}$ aryl, —O—$C_1$-$C_{10}$ alkyl, or —O—$C_5$-$C_{15}$ aryl; and
n is 1 or 2.

In another embodiment, compounds of Formula III include compounds wherein R¹ is optionally substituted $C_1$-$C_{24}$ alkyl. Another group of compounds of Formula III include compounds wherein R¹ is optionally substituted $C_1$-$C_6$ alkyl. Another group of compounds of Formula III include compounds wherein R¹ is optionally substituted methyl, ethyl, or isopropyl. Another group of compounds of Formula III include compounds wherein R¹ is optionally substituted $C_5$-$C_{50}$ aryl. Another group of compounds of Formula III include compounds wherein R¹ is optionally substituted $C_5$-$C_{10}$ aryl. Another group of compounds of Formula III include compounds wherein each of R², R³, and R⁵ is, independently, hydroxyl. Another group of compounds of Formula III include compounds wherein each of R², R³, and R⁵ is, independently, optionally substituted $C_1$-$C_{10}$ alkyl. Another group of compounds of Formula III include compounds wherein each of R², R³, and R⁵ is, independently, optionally substituted $C_1$-$C_6$ alkyl. Another group of compounds of Formula III include compounds wherein each of R², R³, and R⁵ is, independently, optionally substituted methyl, ethyl, or isopropyl. Another group of compounds of Formula III include compounds wherein each of R², R³, and R⁵ is, independently, optionally substituted $C_5$-$C_{15}$ aryl. Another group of compounds of Formula III include compounds wherein each of R², R³, and R⁵ is, independently, optionally substituted $C_5$-$C_{10}$ aryl.

In another embodiment, the invention provides compounds represented by Formula IV:

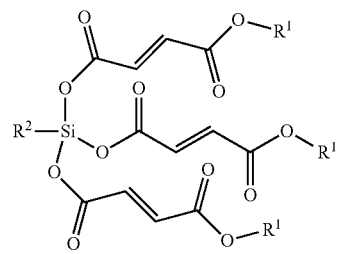

(IV)

or a pharmaceutically acceptable salt thereof, wherein:
R¹ is $C_1$-$C_{24}$ alkyl or $C_5$-$C_{50}$ aryl; and
R² is $C_1$-$C_{10}$ alkyl.

In another embodiment, compounds of Formula IV include compounds wherein R¹ is optionally substituted $C_1$-$C_{24}$ alkyl. Another group of compounds of Formula IV include compounds wherein R¹ is optionally substituted $C_1$-$C_6$ alkyl. Another group of compounds of Formula IV include compounds wherein R¹ is optionally substituted methyl, ethyl, or isopropyl. Another group of compounds of Formula IV include compounds wherein R¹ is optionally substituted $C_5$-$C_{50}$ aryl. Another group of compounds of Formula IV include compounds wherein R¹ is optionally substituted $C_5$-$C_{10}$ aryl. Another group of compounds of Formula IV include compounds wherein R² is optionally substituted $C_1$-$C_6$ alkyl. Another group of compounds of Formula IV include compounds wherein R² is optionally substituted methyl, ethyl, or isopropyl.

The term "alkyl" as employed herein by itself or as part of another group refers to both straight and branched chain radicals of up to 24 carbons. Alkyl groups include straight-chained and branched $C_1$-$C_{24}$ alkyl groups, e.g., $C_1$-$C_{10}$ alkyl groups. $C_1$-$C_{10}$ alkyl groups include methyl, ethyl, propyl, isopropyl, butyl, isobutyl, sec-butyl, tert-butyl, pentyl, isopentyl, neopentyl, hexyl, isohexyl, 3-methylpentyl, 2,2-dimethylbutyl, 2,3-dimethylbutyl, heptyl, 1-methylhexyl, 2-ethylhexyl, 1,4-dimethylpentyl, octyl, nonyl, and decyl. Unless otherwise indicated, all alkyl groups described herein include both unsubstituted and substituted alkyl groups. Further, each alkyl group can include its deuterated counterparts.

The term "aryl" as employed herein by itself or as part of another group refers to monocyclic, bicyclic, or tricyclic aromatic groups containing from 5 to 50 carbons in the ring portion. Aryl groups include $C_{5-15}$ aryl, e.g., phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 3-amino-naphthyl, 2-methyl-3-amino-naphthyl, 6-amino-2-naphthyl, 4,6-dimethoxy-2-naphthyl, indanyl, biphenyl, phenanthryl, anthryl, and acenaphthyl. Unless otherwise indicated, all aryl groups described herein include both unsubstituted and substituted aryl groups.

Optional substituents on the alkyl group include one or more substituents independently selected from halogen, hydroxyl, carboxyl, amino, nitro, or cyano.

Optional substituents on the aryl group include one or more substituents independently selected from alkyl, alkoxy, halogen, hydroxyl, or amino.

Halogen groups include fluorine, chlorine, bromine, and iodine.

Some of the compounds of the present invention may exist as stereoisomers including optical isomers. The invention includes all stereoisomers and both the racemic mixtures of such stereoisomers as well as the individual enantiomers that may be separated according to methods that are well-known to those of ordinary skill in the art.

The compounds of the invention may be prepared using methods known to those skilled in the art, or the novel methods of this invention.

Specifically, the compounds of this invention of Formula I may be prepared by the exemplary reaction in Scheme 1.

Scheme 1

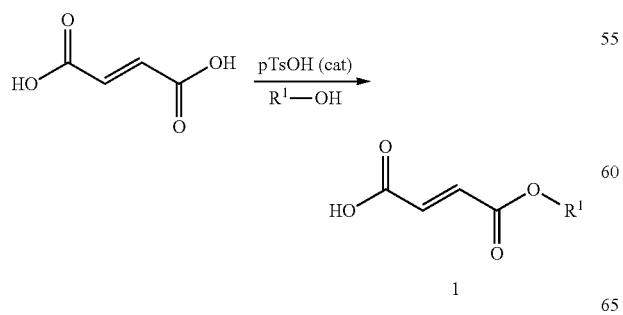

wherein $R^1$, $R^2$, and $R^3$ are each defined above for Formula II.

Reaction of fumaric acid ester 1 with silane diacetate intermediate 2 in a refluxing organic solvent such as diethyl ether, toluene, or hexane to give the desired siloxane 3.

Some of the fumaric acid esters 1 are commercially available. Fumaric acid ester 1 can also be prepared, for example, using synthetic methods known by one of ordinary skill in the art. For example, fumaric acid can be converted by reacting alcohol ($R^1$—OH) with a catalytic amount of p-toluene sulfonic acid at room temperature for a few hours to overnight as shown in Scheme 2.

Scheme 2

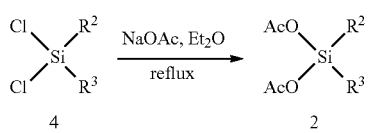

wherein $R^1$ is defined above for Formula I.

Alternatively, fumaric acid ester 1 can be prepared by reacting alcohol ($R^1$—OH) under the coupling conditions of hydroxybenzotriazole (HOBT), 1-ethyl-3-(3-dimethylaminopropyl)carbodiimide (EDCI), and diisopropyl amine (DIPEA) as shown in Scheme 3.

Scheme 3

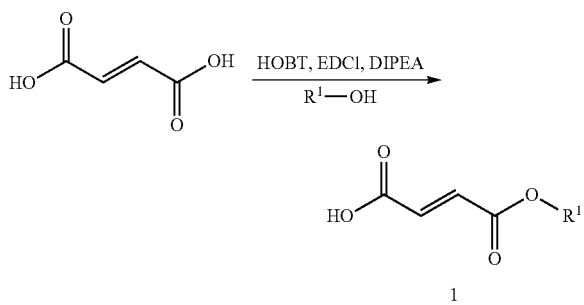

wherein $R^1$ is defined above for Formula I.

Some of the silanes that can be used in the present invention are commercially available. Commercially available silyl halides include trimethylsilyl chloride, dichloromethylphenylsilane, dimethyldichlorosilane, methyltrichlorosilane, (4-aminobutyl)diethoxymethylsilane, trichloro(chloromethyl)silane, trichloro(dichlorophenyl)silane, trichloroethylsilane, trichlorophenylsilane, and trimethylchlorosilane. Commercial sources for silyl halides include Sigma Aldrich and Acros Organics.

Silanes used in the present invention can be prepared, for example, using synthetic methods known by one of ordinary skill in the art. For example, trichlorosilane may be prepared by the exemplary reaction in Scheme 4.

Scheme 4

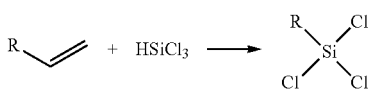

The silylation of styrene derivatives catalyzed by palladium is described in Zhang, F. and Fan, Q.-H., *Organic & Biomolecular Chemistry* 7:4470-4474 (2009) and in Bell, J. R., et al., *Tetrahedron* 65:9368-9372 (2009).

Diacetate intermediate 2 may be prepared by treatment of dichlorosubstituted silicon compound 4 with sodium acetate in diethyl ether under reflux as shown in Scheme 5.

Scheme 5 wherein $R^2$ and $R^3$ are each defined above for Formula I.

Specifically, the compounds of this invention of Formula III may be prepared by the exemplary reaction in Scheme 6.

Scheme 6

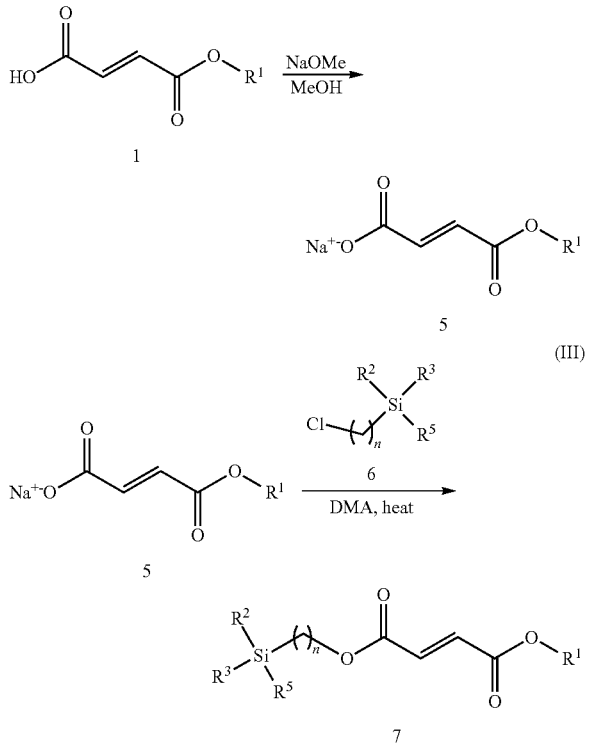

wherein $R^1$, $R^2$, $R^3$, and $R^5$ are as defined above for Formula III.

Fumaric acid ester 1 can be converted to the sodium salt 5 using, for example, sodium methoxide in methanol at room temperature. Removal of the solvent would afford sodium salt 5. Treatment of the sodium salt 5 with silane 6 in an organic solvent such as dimethylformamide under reflux would generate ester 7. The synthesis of structurally related (trimethoxysilyl)-methyl esters is described in Voronkov, M. G., et al., *Zhurnal Obshchei Khimii* 52:2052-2055 (1982).

Alternatively, the compounds of this invention of Formula III may be prepared by the exemplary reaction in Scheme 7.

Scheme 7

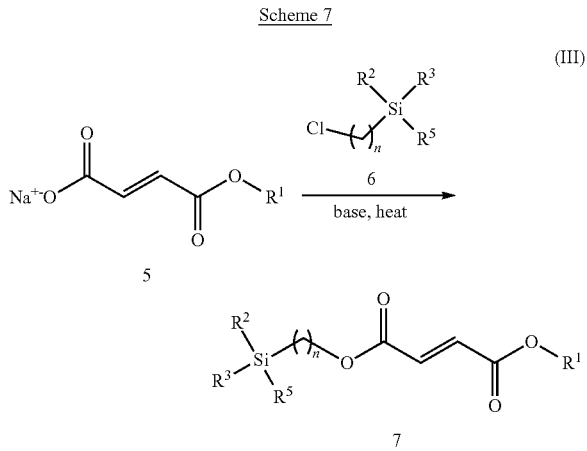

wherein $R^1$, $R^4$, $R^5$, $R^6$, and n are as defined above for Formula III.

Treatment of the sodium salt 5 with silane 6 in an organic solvent such as dimethylformamide under heating with or without an acid scavenger would generate ester 7.

Scheme 8

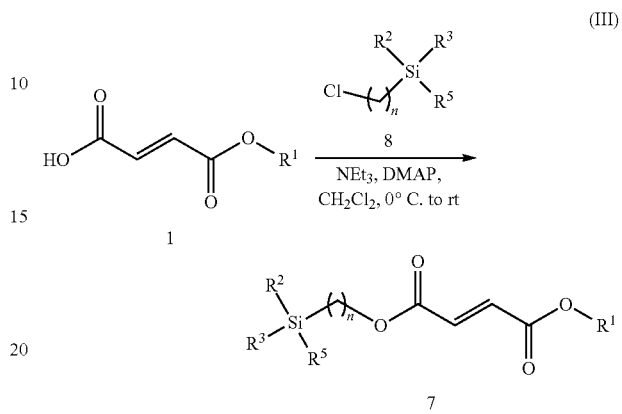

wherein $R^1$, $R^4$, $R^5$, $R^6$, and n are as defined above for Formula III.

Reaction of fumaric acid ester 1 with tri-substituted silane alcohol 8 in methylene chloride with mild base such as triethyl amine and 4-N,N-dimethyl amino pyridine (DMAP) at room temperature generates fumarate 7. See Coelho, P. J., et al., *Eur. J. Org. Chem.* 3039-3046 (2000).

Specifically, the compounds of this invention of Formula IV can be prepared by the exemplary reaction in Scheme 9.

Scheme 9

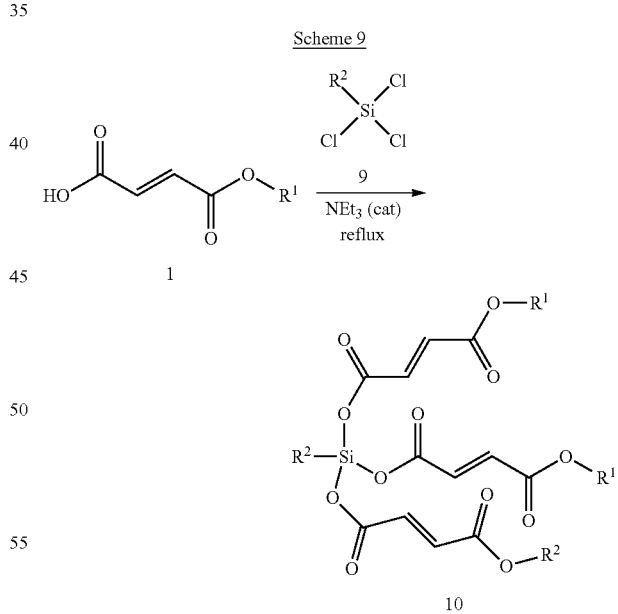

wherein $R^1$ and $R^2$ are as defined above for Formula IV.

Reaction of fumaric acid 1 with trichlorosilane 9 in a refluxing organic solvent such as hexane or toluene using a catalytic amount of a base such as triethylamine generates the trifumarate silane 10. The reaction of acetic and methacrylic acids with 1-silyladamantanes is described in Fedotov, N. S., et al., *Zhurnal Obshchei Khimii* 52:1837-1842 (1982).

The present invention includes a therapeutic method comprising administering to an animal an effective amount of a compound of Formulae I-IV, or a pharmaceutically acceptable salt of said compound of Formulae I-IV, wherein said therapeutic method is useful for treating a subject having a condition or at risk of having a condition characterized by at least one symptom chosen from neurodegeneration and neuroinflammation. A condition characterized by at least one of neurodegeneration and neuroinflammation is a condition in which either or both of those processes leads to a failure of the subjects nervous system to function normally. The loss of normal function may be located in either or both of the central nervous system or it can affect the immune system in general (e.g., the brain or spinal cord) and the peripheral nervous system or it can affect the immune system in general (e.g., in circulation and in tissues). Examples of such conditions include, but are not limited to, Adrenal Leukodystrophy (ALD), Alcoholism, Alexander's disease, Alper's disease, Alzheimer's disease, Amyotrophic lateral sclerosis (ALS or Lou Gehrig's Disease), Ataxia telangiectasia, Batten disease (also known as Spielmeyer-Vogt-Sjörgren-Batten disease), Bovine spongiform encephalopathy (BSE), Canavan disease, Cerebral palsy, Cockayne syndrome, Corticobasal degeneration, Creutzfeldt-Jakob disease, Familial Fatal Insomnia, Fronto-temporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primay lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia, Spinal muscular atrophy, Steele-Richardson-Olszewski disease, Tabes dorsalis, Toxic encephalopathy, LHON (Leber's Hereditary optic neuropathy), MELAS (Mitochondrial Encephalomyopathy; Lactic Acidosis; Stroke), MERRF (Myoclonic Epilepsy; Ragged Red Fibers), PEO (Progressive External Opthalmoplegia), Leigh's Syndrome, MNGIE (Myopathy and external ophthalmopolegia; Neuropathy; Gastro-Intestinal; Encephalopathy), Kearns-Sayre Syndrome (KSS), NARP, Hereditary Spastic Paraparesis, Mitochondrial myopathy, and Friedreich Ataxia.

In one embodiment, the condition is multiple sclerosis. In another embodiment, the condition is relapsing-remitting multiple sclerosis. In another embodiment, the condition is secondary-progressive multiple sclerosis. In another embodiment, the condition is primary-progressive multiple sclerosis. In another embodiment, the condition is progressive-relapsing multiple sclerosis.

In one embodiment, the condition is Amyotrophic lateral sclerosis (ALS).

In one embodiment, the condition is Huntington's disease.

In one embodiment, the condition is Parkinson's disease.

In one embodiment, the condition is Alzheimer's disease.

In some embodiments, administration of at least one compound or pharmaceutically acceptable salt thereof, as described herein, to a patient gives rise to "neuroprotection," or said another way, the effect of administering the compound to the patient is neuroprotection. Neuroprotection comprises at least one of maintenance, salvage, recovery, and regeneration of the nervous system, its cells, structure, and function following injury or damage. In some embodiments, neuroprotection comprises at least one of primary neuroprotection and secondary neuroprotection. "Primary neuroprotection" is protection comprising direct modulation of the structure and/or function of neural cells residing within the CNS (at least one cell type selected from neurons, oligodendrocytes, astrocytes, and microglia). "Secondary neuroprotection" is protection comprising modulation of the structure or function of at least one cell type that typically resides outside the CNS (e.g. immune cells). In secondary neuroprotection, the at least one compound or pharmaceutically acceptable salt thereof acts directly or indirectly on the at least one cell type that typically resides outside the CNS to modulate the structure and/or function of the at least one cell type. The at least one cell type then modulates, directly or otherwise, the structure and/or function of neural cells residing within the CNS (at least one cell type selected from neurons, oligodendrocytes, astrocytes, and microglia). In some embodiments, neuroprotection comprises a lessening of the severity or rate of neurodegeneration or neuroinflammation in a subject. "Maintenance" of the nervous system, its cells, structure, and function comprises embodiments in which the at least one compound or pharmaceutically acceptable salt thereof is administered to a subject prior to development of at least one sign or symptom of a disease or condition disclosed herein and reduces the eventual severity of the disease or condition and/or reduces the rate of onset of the disease and/or condition.

In some embodiments, the condition to be treated is characterized by increased expression of pro-inflammatory genes, such as in neural cells of the subject. In the case of a subject experiencing astrogliosis, for example, expression of at least one pro-inflammatory gene selected from Ccl20, Ccl3, Ccl4, Cxcl1, Cxcl10, Cxcl2, Cxcl3, Cxcl6, IL1a, Il1b, TNF, Ifit3, Nfkbia, Nfkbiz, Tnfaip2, and Zc3h12a is increased in the subject. In some embodiments, administration of at least a compound, or a pharmaceutically acceptable salt thereof, as described herein, to the subject, results in suppression of expression of at least one gene selected from Ccl20, Ccl3, Ccl4, Cxcl1, Cxcl10, Cxcl2, Cxcl3, Cxcl6, IL1a, Il1b, TNF, Ifit3, Nfkbia, Nfkbiz, Tnfaip2, and Zc3h12a.

Certain examples of neuroprotective genes are also disclosed herein, namely Gsta2, Gsta3, Gclc, Ggt1, Txnrd1, Srxn1, Sqstm1, and NQO1. In some embodiments, administration of at least one compound or pharmaceutically acceptable salt thereof, as described herein, to the subject, results in an up-regulation of at least one gene selected from Gsta2, Gsta3, Gclc, Ggt1, Txnrd1, Srxn1, Sqstm1, and NQO1.

The term "therapeutically effective amount" refers to that amount of a compound or pharmaceutically acceptable salt thereof which results in prevention or delay of onset or amelioration of at least one symptom of a condition characterized by neurodegeneration or neuroinflammation in a subject, or an attainment of a desired biological outcome, such as reduced astrogliosis.

In some embodiments, the expression level of at least one gene selected from Ccl20, Ccl3, Ccl4, Cxcl1, Cxcl10, Cxcl2, Cxcl3, Cxcl6, IL1a, Il1b, TNF, Ifit3, Nfkbia, Nfkbiz, Tnfaip2, Zc3h12a, Gsta2, Gsta3, Gclc, Ggt1, Txnrd1, Srxn1, Sqstm1, and NQO1 is measured in a subject. In some embodiments, expression of the gene is measured by determining the expression level of an mRNA for that gene. In some embodiments, expression of the gene is measured by determining the expression level of a protein product encoded by the gene. In some embodiments, the protein product is measured in cerebrospinal fluid or blood (e.g., plasma) of the subject. In some embodiments, expression level is measured at least at one time point selected from prior to initiation of treatment, during treatment, and after treatment.

The ability of compounds of the present invention to activate the Nrf-2 antioxidant response pathway can be tested according to Example 5 below. The compounds can also be evaluated in other cell based assays or animal model(s) of neuroinflammatory and neurodegenerative diseases. For example, compounds of the present invention can be evaluated for their ability to treat ALS in a cell-based motor neuron survival assay as described in Haidet-Phillips et al., *Nat Biotechnol.* 29(9):824-828 (2011). For animal model studies, compounds of the present invention can be investigated in models for Alzheimer's disease (see Dumont et al., *J. Neurochem.* 109(2):502-512 (2009)), Parkinson's disease (see Jakel et al., *Brain Res.* 1144:192-201 (2007)), ALS (see Wegorzewska et al., *Proc. Natl. Acad. Sci. USA.* 106(44):18809-14 (2009); Wong et al., Neuron 14(6):1105-1116 (1995); and Vargas et al., *J. Neurosci.* 28(50):13574-13581 (2008)), Huntington's disease (see Stack et al., *Free Radic. Biol. Med.* 49(2):147-158 (2010)), and MS (the Experimental Autoimmune Encephalomyelitis (EAE) model; see, e.g., Tuohy et al., *J. Immunol.* 141:1126-1130 (1988), Sobel et al., *J. Immunol.* 132:2393-2401 (1984), and Traugott, *Cell Immunol.* 119:114-129 (1989)).

The term "treating" refers to administering a therapy in an amount, manner, and/or mode effective to prevent or delay onset of or amelioration of at least one symptom of a condition characterized by neurodegeneration or neuroinflammation in a subject, to either a statistically significant degree or to a degree detectable to one skilled in the art. An effective amount, manner, or mode can vary depending on the subject and may be tailored to the subject. For neurological disorders referred herein, the treatment offered by the method of this invention aims at improving the conditions (or lessening the detrimental effects) of the disorders and not necessarily at completely eliminating or curing the disorders.

The compounds and pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The amount of active ingredient that can be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient can also depend upon the therapeutic or prophylactic agent, if any, with which the ingredient is co-administered.

In some embodiments, the compounds and pharmaceutical compositions of the invention can be administered in an amount ranging from about 1 mg/kg to about 50 mg/kg (e.g., from about 2.5 mg/kg to about 20 mg/kg or from about 2.5 mg/kg to about 15 mg/kg). The amount of the compounds and pharmaceutical compositions of the invention administered will also vary, as recognized by those skilled in the art, dependent on route of administration, excipient usage, and the possibility of co-usage with other therapeutic treatments including use of other therapeutic agents.

For example, the compounds and pharmaceutical compositions of the invention can be administered to a subject, for example orally, in an amount of from about 0.1 g to about 1 g per day, or for example, in an amount of from about 100 mg to about 800 mg per day.

The amount of compounds and pharmaceutical compositions of the invention may be administered in separate administrations of 2, 3, 4, 5 or 6 equal doses per day.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which may be used pharmaceutically. For example, the preparations, particularly those preparations which may be administered orally and which may be used for the preferred type of administration, such as tablets, dragees, and capsules, and also preparations which may be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the compound of Formulae I-IV with a solution of a pharmaceutically acceptable non-toxic acid such as hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, gluconate, glucaronate, saccharate, formate, benzoate, glutamate, methanesulfonate, ethanesulfonate, benzenesulfonate, p-toluenesulfonate, and pamoate. Acceptable base salts include aluminum, calcium, lithium, magnesium, potassium, sodium, zinc, and diethanolamine salts.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

In one embodiment, the pharmaceutical preparations comprise a capsule containing the compound or pharmaceutical composition of the present invention in the form of an enteric-coated microtablet. The coating of the microtablet may be composed of different layers. The first layer may be a methyacrylic acid—methyl methacrylate copolymer/isopropyl solution which isolates the tablet cores from potential hydrolysis from the next applied water suspensions. The enteric coating of the tablet may then be conferred by an aqueous methacrylic acid—ethyl acrylate copolymer suspension.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400), or cremophor, or cyclodextrins. Aqueous injection suspensions may contain substances which increase the viscosity of the suspension and include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of psoriasis. The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations.

Creams are preferably formulated from a mixture of mineral oil, self-emulsifying beeswax and water in which mixture the active ingredient, dissolved in a small amount of oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Having now generally described this invention, the same will be understood by reference to the following examples which are provided herein for purposes of illustration only and are not intended to be limiting unless otherwise specified.

EXAMPLES

Example 1

Synthesis of (E)-O,O'-(dimethylsilanediyl)dimethyl difumarate (Compound 11)

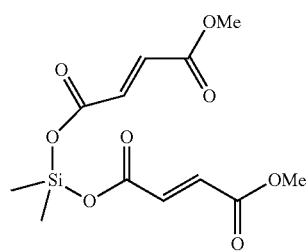

Step 1: Preparation of Dimethylsilanediyl Diacetate 11B

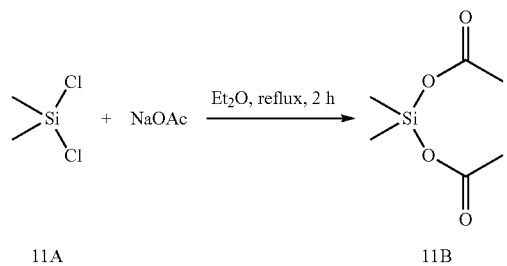

To a slurry of sodium acetate (8.2 g, 100 mmol, 2.0 equiv.) in anhydrous diethyl ether (40 mL) was slowly added a solution of dimethyldichloro silane 11A (6.45 g, 50 mmol, 1.0 equiv.) in anhydrous diethyl ether (10 mL). After addition was completed, the mixture was heated at reflux for 2 hours, and then filtered under $N_2$. The filtrate was concentrated under vacuum at 40° C. to give diacetate 11B as a colorless oil (6.1 g, 70%).

¹H NMR (400 MHz, CDCl₃) δ ppm: 2.08 (s, 6H), 0.48 (s, 6H).

Step 2: Preparation of (E)-O,O'-(dimethylsilanediyl)dimethyl difumarate 11

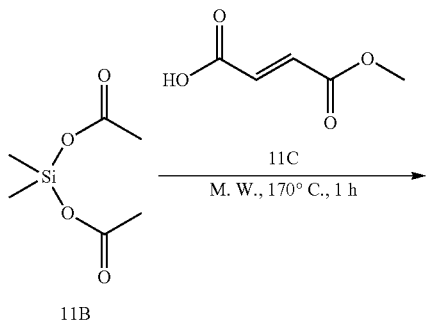

A mixture of 11B (2.0 mL, 12 mmol, 1.5 equiv.) and 11C (1.04 g, 8.0 mmol, 1.0 equiv.) in a sealed tube was heated at 170° C. with stirring under microwave condition for 1 hour. After cooling to 50° C., the mixture was transferred to a round bottom flask and the excess silica reactant 11B was removed under vacuum at 100° C. to afford compound 11 as brown oil (1.47 g, 60%). ¹H NMR (400 MHz, CDCl₃) δ ppm: 6.82-6.80 (m, 4H), 3.79 (s, 6H), 0.57 (s, 6H).

Example 2

Synthesis of methyl ((trimethoxysilyl)methyl) fumarate (Compound 12)

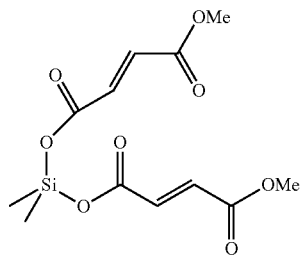

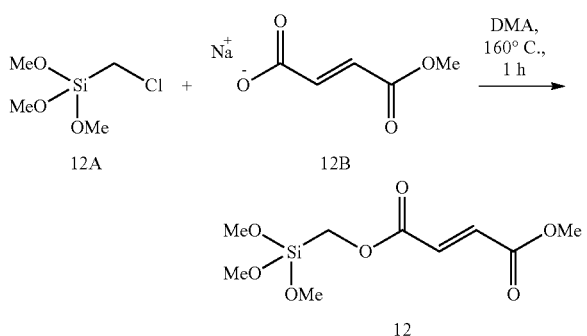

To a stirred solution of monomethyl fumarate (3.5 g, 27 mmol, 1.0 equiv.) in anhydrous THF (35 mL) at room temperature was added sodium hydride (1.08 g, 27 mmol, 1.0 equiv.) in small portions. After addition, the mixture was heated to reflux for 3 hours, and then cooled to room temperature. The solid was collected by filtration and washed twice with diethyl ether, and further dried in vacuo to give 3.8 g of 12B (93%).

To a suspension of 12B (760 mg, 5.0 mmol, 1.0 equiv.) in dry DMA (5 mL) at 100° C. under nitrogen was added a solution of 12A (1.03 g, 6.0 mmol, 1.2 equiv.) in dry DMA (1 mL) dropwise. The resulting mixture was heated to 160° C. and stirred for 1 hour, and then cooled to room temperature. The solid was filtered, and the filtrate was evaporated under reduced pressure to give the titled compound 12, 513 mg (37%), as a red viscous liquid.

¹H NMR (400 MHz, CDCl₃) δ ppm: 6.90-6.86 (m, 2H), 3.97 (s, 2H), 3.82 (s, 3H), 3.62 (s, 9H).

Example 3

Synthesis of methyl ((trihydroxysilyl)methyl) fumarate (Compound 13)

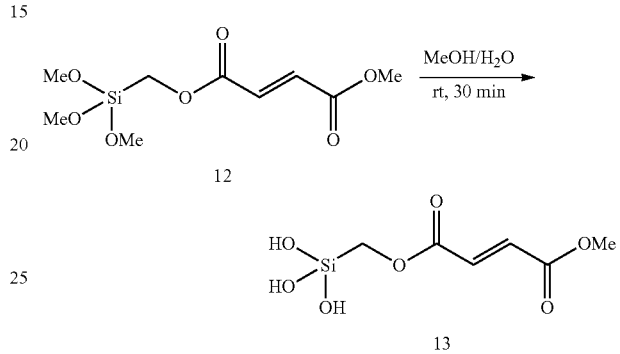

To a solution of 12 (1.0 g, 3.8 mmol, 1.0 equiv., prepared in Example 2) in MeOH (10 mL) at room temperature was added water (341 mg, 19.0 mmol, 5.0 equiv.) dropwise. After addition, the mixture was stirred at room temperature for 30 minutes, with white solids precipitated out. The solids were collected through filtration, washed with methanol three times, and dried at 60° C. in vacuo, to provide the titled compound 13, 500 mg (59%), as a white solid.

¹H NMR (400 MHz, DMSO-d6) δ ppm: 6.79-6.74 (m, 2H), 3.91-3.58 (m, 6H), 3.18-3.15 (m, 2H).

Example 4

Synthesis of trimethyl (methylsilanetriyl)trifumarate (Compound 14)

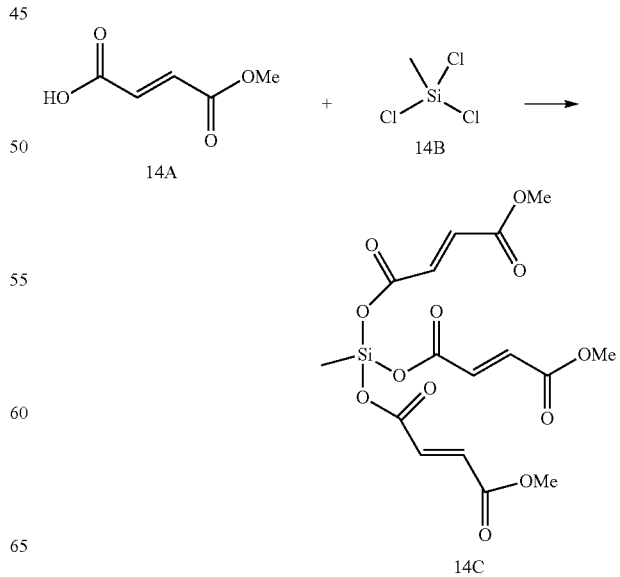

Following the procedure described in Scheme 9, monomethyl fumarate 14A would react with trichloromethanesilane 14B in refluxing toluene or hexanes with a catalytic amount of triethylamine to provide (2'E, 2"E)-trimethyl O,O',O"-(methylsilanetriyl)trifumarate 14C.

Example 5

Nrf2 Activation Cell-Based Assay

Human cancer cell line DLD-1 and breast cancer cell line MCF7 reporter stable cell lines were generated by transfection with a firefly luciferase reporter construct harboring the luciferase cDNA cloned downstream of eight catenated copies of the antioxidant response element (ARE: SEQ ID NO.:1).

To measure Nrf2 activation in the ARE-luciferase reporter cell lines, the cells were plated in 96-well plates at 20-50 k cells/well 24 hours prior to stimulation with the test compounds. The test compounds were prepared in dimethylsulfoxide (DMSO) and diluted with culture media to required concentrations (final DMSO concentrations <0.3%). The reporter cells were harvested 24 hours-48 hours after addition of the compounds and lysed for detection of luciferase activity. Luciferase activity in the lysates was monitored using the Bright-Glo Luciferase Assay System of Promega and Tecan Genios Pro plate reader.

Luciferase induction in the compound-treated cells was calculated as fold change over the baseline activity detected in control cultures treated with DMSO-containing media.

TABLE 1

| | \multicolumn{4}{c}{Maximum Nrf2 Activation Fold Change upon Compound Stimulation} | | | | |
|---|---|---|---|---|---|---|---|---|
| | \multicolumn{4}{c}{24 hr Stimulation} | \multicolumn{4}{c}{48 hr Stimulation} | |
| | DLD-1/ARE-E2 | | MCF7/ARE-D3 | | DLD-1/ARE-E2 | | MCF7/ARE-D3 | |
| | Fold Change | @ [uM] | Fold Change | @ [uM] | Fold Change | @ [uM] | Fold Change | @ [uM] |
| DMF | 11 | 31 | 24 | 94 | 13 | 47 | 45 | 94 |
| MMF | 7 | 1000 | 56 | 1000 | 14 | 1000 | 88 | 1000 |
| Compound 11 | 42 | 1000 | 97 | 750 | 43 | 1000 | 126 | 500 |
| Compound 12 | 24 | 250 | 49 | 500 | 48 | 375 | 65 | 500 |

Table 1 indicates that Compound 11 and Compound 12 are able to activate ARE-dependent signaling of the luciferase reporter construct. This suggests the compounds are able to activate the Nrf2 signaling cascade and induce expression of genes downstream of the ARE.

Example 6

In Vivo Evaluation of Nrf2 Activation

Test compounds were dosed either in suspension of 0.8% HPMC or corn oil via oral gavage to male SD rats (average weight of 250 mg, 6 animals per group, two groups), at a dose of 100 mg/kg equivalent of DMF (dosing volume: 5 ml/kg). After 30 minutes, the first group of animals was sacrificed via $CO_2$ asphyxiation. 1.0 mL blood sample via cardiac bleed pipetted into chilled lithium heparin tubes with 10 mg sodium fluoride. Samples were centrifuged within 30 minutes at 4° C. for 15 minutes at 1500G and plasma was transferred to chilled tubes and immediately frozen on dry ice, further kept at −70° C. until shipment for analysis. Brain was removed; sections were weighed and frozen until analysis. Brain and plasma samples were analyzed for monomethylfumaric acid ester (MMF) exposure. After 6 h, the second group of animals was sacrificed via CO2 asphyxiation. Brain, spleen, liver and jejunum were removed, flash frozen and placed on dry ice and maintained frozen until analysis. Sections of brain, spleen, liver, and jejunum were submitted for qPCR analysis of relative expression increase of Nrf2 responsive enzymes such as NQO-1, Akr1b8, and Sulfiredoxin-1.

Having now fully described this invention, it will be understood by those of ordinary skill in the art that the same can be performed within a wide and equivalent range of conditions, formulation and other parameters without affecting the scope of the invention or any embodiment thereof. All patents, patent applications and publications cited herein are fully incorporated by reference herein in their entirety.

What is claimed is:

1. A compound having Formula II:

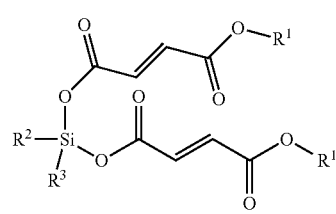

(II)

or a pharmaceutically acceptable salt thereof, wherein:
$R^1$ is $C_1$-$C_{24}$ alkyl or $C_6$-$C_{10}$ aryl; $R^1$ being unsubstituted;
each of, independently, $R^2$ and $R^3$, is $C_1$-$C_{10}$ alkyl or $C_6$-$C_{10}$ aryl;
$R^2$ and $R^3$ are the same or different, and are optionally substituted.

2. The compound of claim 1, wherein each of $R^2$ and $R^3$, independently, is methyl, ethyl, or isopropyl.

3. The compound of claim 1, wherein $R^1$ is methyl, ethyl, or isopropyl.

4. A compound having Formula IV:

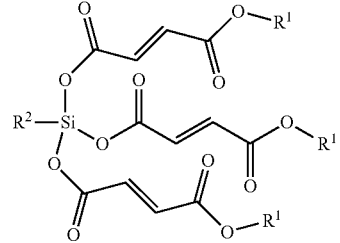

(IV)

or a pharmaceutically acceptable salt thereof, wherein:
$R^1$ is $C_1$-$C_{24}$ alkyl or $C_6$-$C_{10}$ aryl; and
$R^2$ is $C_1$-$C_{10}$ alkyl.

5. The compound of claim 4, wherein $R^2$ is methyl, ethyl, or isopropyl.

6. The compound of claim 4, wherein each $R^1$, independently, is methyl, ethyl, or isopropyl.

7. The compound of claim 2, wherein the compound is (E)-O,O'-(dimethylsilanediyl)dimethyl difumarate.

8. The compound of claim 4, wherein the compound is trimethyl (methylsilanetriyl) trifumarate.

* * * * *